(12) United States Patent
Heraty et al.

(10) Patent No.: US 9,597,214 B2
(45) Date of Patent: Mar. 21, 2017

(54) MEDICAL DEVICE

(76) Inventors: Kevin Heraty, Castlebar (IE); Liam Mullins, Athlone (IE); Paul Gilson, Moycullen (IE); Martin Burke, Tuam (IE)

( * ) Notice: Subject to any disclaimer, the term of this patent is extended or adjusted under 35 U.S.C. 154(b) by 162 days.

(21) Appl. No.: 12/249,448

(22) Filed: Oct. 10, 2008

(65) Prior Publication Data

US 2010/0094403 A1 Apr. 15, 2010

(51) Int. Cl.
 *A61F 2/06* (2013.01)
 *A61F 2/958* (2013.01)
 *A61F 2/30* (2006.01)
 *A61M 25/10* (2013.01)

(52) U.S. Cl.
 CPC ........ *A61F 2/958* (2013.01); *A61F 2002/068* (2013.01); *A61F 2002/3008* (2013.01); *A61F 2002/30289* (2013.01); *A61F 2230/0091* (2013.01); *A61F 2250/0098* (2013.01); *A61M 25/1011* (2013.01)

(58) Field of Classification Search
 CPC ............. A61M 29/00; A61B 17/12172; A61B 17/12022; A61B 17/12031; A61B 17/12145
 USPC ................................ 623/1.11, 1.15; 606/191
 See application file for complete search history.

(56) References Cited

U.S. PATENT DOCUMENTS

| | | | |
|---|---|---|---|
| 4,596,548 A | 6/1986 | DeVries et al. | |
| 4,604,762 A | 8/1986 | Robinson | |
| 5,156,619 A | 10/1992 | Ehrenfeld | |
| 5,295,959 A | 3/1994 | Gurbel et al. | |

(Continued)

FOREIGN PATENT DOCUMENTS

| | | |
|---|---|---|
| EP | 0 275 230 A2 | 7/1988 |
| EP | 0 696 447 A2 | 2/1996 |

(Continued)

OTHER PUBLICATIONS

International Search Report of International Application No. PCT/GB2009/002433 dated Jan. 19, 2010 (English Text).

(Continued)

*Primary Examiner* — Thomas J Sweet
*Assistant Examiner* — Tiffany Shipmon

(57) ABSTRACT

A stent deployment device comprises an elongate catheter shaft (2), and an inflatable balloon (3). The inflatable balloon (3) is movable between a collapsed configuration and an expanded configuration. In the expanded configuration part of the longitudinal axis of the balloon (3) is curved in three-dimensional space, and part of the balloon (3) is helically shaped. A stent (6) is movable from a collapsed delivery configuration to a partially expanded intermediate configuration, and subsequently from the intermediate configuration to a fully expanded deployed configuration. In the delivery configuration the longitudinal axis of the stent (6) is straight. The longitudinal axis of the stent (6) may be straight or curved in three-dimensional space in the intermediate configuration. In the deployed configuration the longitudinal axis of the stent (6) is curved in three-dimensional space. The balloon (3) in the expanded configuration exerts force on the stent (6). In the deployed configuration the stent (6) in turn exerts force on the internal wall of a blood vessel (5) causing the longitudinal axis of the blood vessel (5) to curve in three-dimensional space.

24 Claims, 11 Drawing Sheets

(56) References Cited

U.S. PATENT DOCUMENTS

| | | |
|---|---|---|
| 5,308,356 A | 5/1994 | Blackshear, Jr. et al. |
| 5,370,691 A | 12/1994 | Samson |
| 5,383,856 A | 1/1995 | Bersin |
| 5,484,411 A | 1/1996 | Inderbitzen et al. |
| 5,545,132 A | 8/1996 | Fagan et al. |
| 5,569,191 A | 10/1996 | Meyer |
| 5,596,990 A | 1/1997 | Yock et al. |
| 5,618,299 A | 4/1997 | Khosravi et al. |
| 5,649,978 A | 7/1997 | Samson |
| 5,653,745 A | 8/1997 | Trescony et al. |
| 5,670,161 A | 9/1997 | Healy et al. |
| 5,733,327 A | 3/1998 | Igaki et al. |
| 5,735,816 A | 4/1998 | Lieber et al. |
| 5,800,456 A | 9/1998 | Maeda et al. |
| 5,865,723 A | 2/1999 | Love |
| 6,039,754 A | 3/2000 | Caro |
| 6,152,139 A | 11/2000 | Laufer |
| 6,364,904 B1 | 4/2002 | Smith |
| 6,375,660 B1 | 4/2002 | Fischell |
| 6,425,908 B2 | 7/2002 | Ravenscroft et al. |
| 6,527,739 B1 | 3/2003 | Bigus et al. |
| 6,896,007 B2 | 5/2005 | Cymbalisty |
| 7,766,871 B2 | 8/2010 | Hirszowicz et al. |
| 2001/0049549 A1 | 12/2001 | Boylan et al. |
| 2002/0022877 A1 | 2/2002 | Mueller et al. |
| 2002/0035390 A1 | 3/2002 | Schaldach et al. |
| 2002/0049487 A1 | 4/2002 | Lootz et al. |
| 2002/0077693 A1 | 6/2002 | Barclay et al. |
| 2002/0116044 A1 | 8/2002 | Cottone |
| 2002/0179166 A1 | 12/2002 | Houston et al. |
| 2003/0163154 A1* | 8/2003 | Miyata ............. A61M 25/1002 606/192 |
| 2004/0039443 A1 | 2/2004 | Solem et al. |
| 2006/0047334 A1 | 3/2006 | Houston et al. |
| 2006/0122554 A1 | 6/2006 | Wilk |
| 2006/0124187 A1 | 6/2006 | Houston et al. |
| 2007/0112407 A1 | 5/2007 | Mertens et al. |
| 2007/0156078 A1 | 7/2007 | Caro et al. |
| 2007/0213663 A1 | 9/2007 | Wang |
| 2008/0306440 A1* | 12/2008 | Hirszowicz et al. ...... 604/99.01 |

FOREIGN PATENT DOCUMENTS

| | | |
|---|---|---|
| EP | 0 699 423 A2 | 3/1996 |
| EP | 0 714 640 | 6/1996 |
| EP | 0 581 900 B1 | 2/1998 |
| EP | 0 612 536 B1 | 12/1999 |
| EP | 1 042 997 A1 | 10/2000 |
| EP | 1 127 557 A1 | 8/2001 |
| EP | 1254645 A1 | 11/2002 |
| EP | 1 269 935 A2 | 1/2003 |
| EP | 1 270 040 | 1/2003 |
| EP | 1 279 382 A1 | 1/2003 |
| EP | 2 292 183 A1 | 3/2011 |
| FR | 2 248 015 A1 | 5/1975 |
| FR | 2 657 945 A3 | 8/1991 |
| FR | 2 666 502 A1 | 3/1992 |
| GB | 2 092 894 A | 8/1982 |
| GB | 2 298 577 A | 9/1996 |
| GB | 2 344 053 A | 5/2000 |
| GB | 2 425 485 | 11/2006 |
| JP | 07-507697 | 8/1995 |
| JP | 08-215317 | 8/1996 |
| JP | 08-257139 | 10/1996 |
| JP | H11-506628 A | 6/1999 |
| JP | 2001-252987 | 9/2001 |
| JP | 2003-528689 A | 9/2003 |
| JP | 2005-103321 A | 4/2005 |
| JP | 2006-520630 | 9/2006 |
| WO | WO 95/09585 A1 | 4/1995 |
| WO | WO 95/17223 A1 | 6/1995 |
| WO | WO 95/35072 A2 | 12/1995 |
| WO | WO 97/24081 A1 | 7/1997 |
| WO | WO 98/26731 A2 | 6/1998 |
| WO | WO 98/26731 A3 | 6/1998 |
| WO | WO 98/53764 A2 | 12/1998 |
| WO | WO 99/17682 A1 | 4/1999 |
| WO | WO 00/32241 A1 | 6/2000 |
| WO | WO 00/38591 A | 7/2000 |
| WO | WO 00/38591 A2 | 7/2000 |
| WO | WO 00/38591 A3 | 7/2000 |
| WO | WO 00/48530 | 8/2000 |
| WO | WO 00/49973 A2 | 8/2000 |
| WO | WO 01/45593 A1 | 6/2001 |
| WO | WO 01/74270 A2 | 10/2001 |
| WO | WO 01/89420 A2 | 11/2001 |
| WO | WO 02/066095 | 8/2002 |
| WO | WO 02/098325 A2 | 12/2002 |
| WO | WO 03/000157 A1 | 1/2003 |
| WO | WO 03/045278 A1 | 6/2003 |
| WO | WO 03/103540 A1 | 12/2003 |
| WO | WO 2004/047908 A2 | 6/2004 |
| WO | WO 2004/066852 A2 | 8/2004 |
| WO | WO 2004/082533 | 9/2004 |
| WO | WO 2004/082533 A1 | 9/2004 |
| WO | WO 2008/117256 | 10/2008 |

OTHER PUBLICATIONS

European Search Report corresponding to EP 08 25 3309, Jan. 19, 2009 (English Text).

Min Invas Ther & Allied Technol 2002: 11(4) pp. 173-178, Entitled: A Comparison of Balloon- and Self-Expanding Stents.

Min Invas Ther & Allied Technol 2002: 11(4) pp. 137-147, Entitled: A Survey of Stent Designs.

Eur. J. Vasc. Endovasc. Surg 24, pp. 13-22 (2002), Entitled: External Supports and the Prevention of Neointima Formation in Vein Grafts.

European Search Report of corresponding European Application No. EP 10 01 0780 dated Dec. 9, 2010.

Abstract of Caro et al., "Influence of Non-Planar Geometry on Flow Separation" (1998) J. Physiol. 513P, 2P.

\* cited by examiner

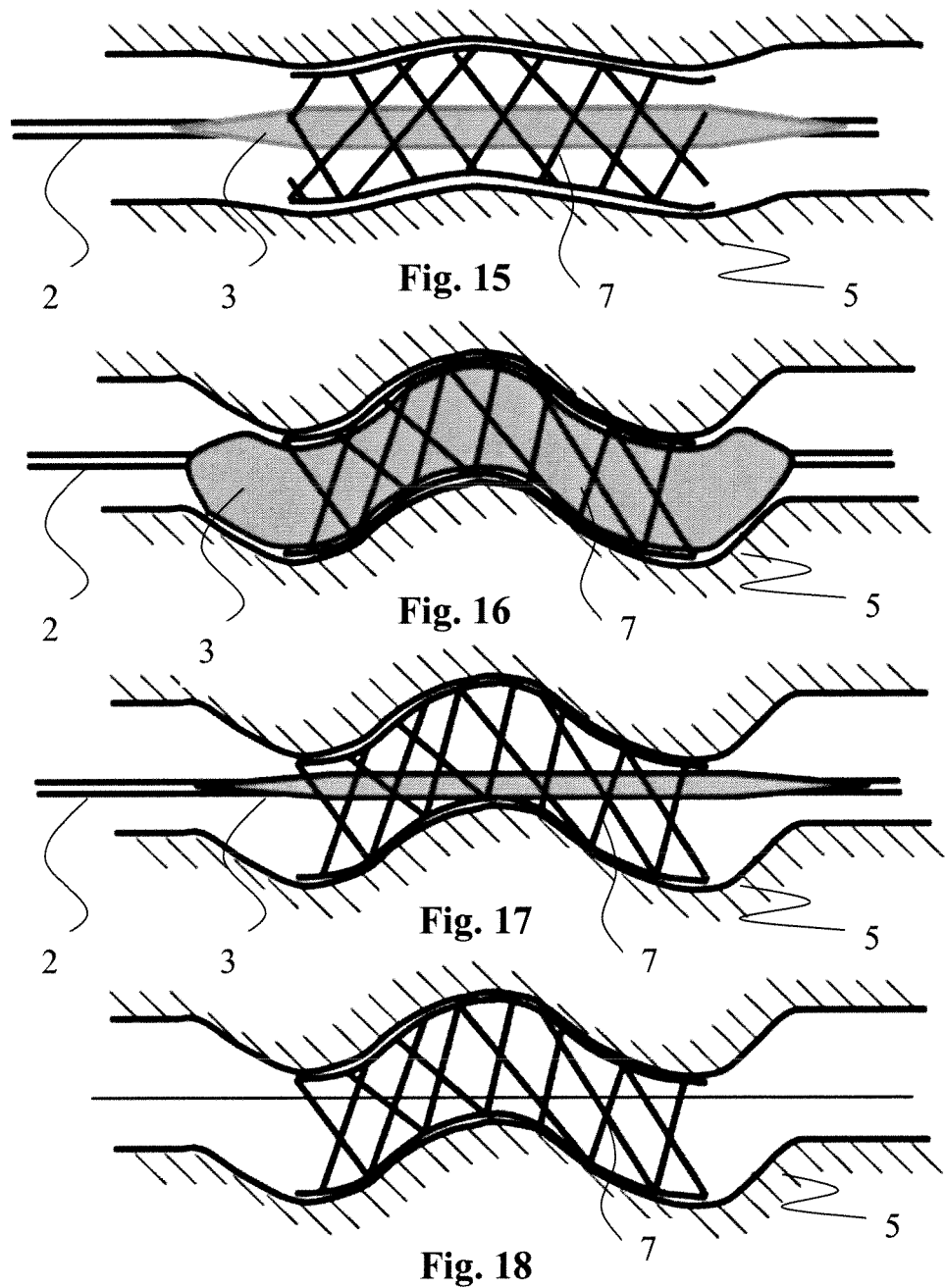

MEDICAL DEVICE

STATEMENT OF INVENTION

According to the invention there is provided a medical device comprising:

an expandable element for location in a blood vessel, the expandable element being movable between a collapsed configuration and an expanded configuration, in the expanded configuration at least part of the longitudinal axis of the expandable element being curved in three-dimensional space.

In one embodiment of the invention in the expanded configuration the expandable element is configured to exert force on the internal wall of a blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of a stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia. Preferably the device comprises a single expandable element.

In one case in the collapsed configuration at least part of the longitudinal axis of the expandable element is substantially straight. This arrangement provides a low-profile for ease of delivery. Preferably in the collapsed configuration at least part of the expandable element is substantially cylindrically shaped. In the expanded configuration at least part of the expandable element may be substantially helically shaped. In the expanded configuration at least part of the expandable element may be substantially spiral shaped.

In some preferred embodiments, at least one longitudinal end part of the expandable element has a helical angle which varies along the length of the end part. Both longitudinal end parts may have this configuration. In certain embodiments the helical angle of the longitudinal axis of an end part of the expandable element increases in a direction away from the end of the element. When a blood vessel is caused by such an expandable element to have a helical longitudinal axis, the end part of the expandable element causes the helical angle of the longitudinal axis of the blood vessel to increase along the length of the end part. Thus a transitional region may be provided in the vessel in which flow in the part of the vessel shaped by the end part of the expandable element is conditioned by the varying helical angle. This arrangement can serve to reduce the area of the internal wall of the blood vessel which has low wall shear stress, to reduce the possibility of recirculation, and to reduce the risk of neointimal hyperplasia. Wall shear stress is generated on the internal wall of a blood vessel by flow adjacent to the wall. Higher levels of wall shear stress have been associated with a reduction in levels of in-stent restenosis.

The expandable element may comprise an inflatable element. Preferably the inflatable element comprises a balloon. The balloon may have one or more longitudinal end parts as discussed above.

The expandable element may be configured to at least partially expand a stent. Preferably in the expanded configuration the expandable element is configured to exert force via a stent on the internal wall of a blood vessel. The expandable element may be configured to expand a stent having a longitudinal axis which curves in three-dimensional space. The expandable element may be configured to expand a stent having a longitudinal axis which is substantially straight. Ideally the device comprises a stent deployment device. Most preferably the device comprises means to align the expandable element with a stent. In the case of a three-dimensional curved stent it is important to ensure the stent is correctly aligned with the three-dimensional curve of the expandable element. The alignment means may comprise means to visualise the expandable element. The alignment means may be arranged to assist rotational alignment of the expandable element with the stent. The alignment means may be arranged to assist axial alignment of the expandable element with the stent. Preferably the alignment means is arranged to assist rotational and axial alignment. Preferably the alignment means comprises one or more markers on the expandable element. Ideally the alignment means extends circumferentially and/or longitudinally along at least part of the expandable element.

In one embodiment in the expanded configuration the expandable element is configured to contact the internal wall of a blood vessel directly. Preferably the device comprises a dilation device.

In one case the device comprises an elongate element upon which the expandable element is mounted.

The device of the invention may be employed as a stent delivery device, and/or as a stent deployment device, and/or as a post dilatation device.

In another aspect of the invention there is provided a medical system comprising:

a medical device of the invention, and a stent suitable for deployment in a blood vessel to support at least part of the internal wall of the blood vessel.

In one embodiment of the invention the stent is movable between a delivery configuration and a deployed configuration. Preferably the stent is collapsed in the delivery configuration. This low-profile arrangement provides for ease of delivery. Ideally in the delivery configuration at least part of the longitudinal axis of the stent is substantially straight. Most preferably the stent is expanded in the deployed configuration. In the deployed configuration at least part of the longitudinal axis of the stent may be curved in three-dimensional space. Preferably in the deployed configuration the stent is configured to exert force on the internal wall of a blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of the stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

In one case the stent is movable between the delivery configuration and an intermediate configuration, and between the intermediate configuration and the deployed configuration. Preferably the stent is at least partially expanded in the intermediate configuration. In the intermediate configuration at least part of the longitudinal axis of the stent may be substantially straight. In the intermediate configuration at least part of the longitudinal axis of the stent may be curved in three-dimensional space.

The invention also provides in another aspect a method for treating a blood vessel, the method comprising the steps of:

locating an expandable element in the blood vessel, and moving the expandable element from a collapsed configuration to an expanded configuration in which at least part of the longitudinal axis of the expandable element is curved in three-dimensional space.

In one embodiment of the invention the expandable element exerts force on the internal wall of the blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of a stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

In one case the step of moving the expandable element from the collapsed configuration to the expanded configuration at least partially expands a stent. Preferably the expandable element exerts force via the stent on the internal wall of the blood vessel. Ideally the method comprises the step of moving the stent from a delivery configuration to a deployed configuration. Most preferably the method comprises the step of moving the stent from the delivery configuration to an intermediate configuration, and from the intermediate configuration to the deployed configuration. The invention may provide a method of deploying a stent. Preferably the method comprises the step of aligning the expandable element with a stent. In the case of a three-dimensional curved stent it is important to ensure the stent is correctly aligned with the three-dimensional curve of the expandable element.

In another embodiment the expandable element contacts the internal wall of the blood vessel directly. The invention may provide a method of dilation.

BRIEF DESCRIPTION OF THE DRAWINGS

The invention will be more clearly understood from the following description of some embodiments thereof, given by way of example only, with reference to the accompanying drawings, in which:

FIGS. 15 to 18 are cross-sectional side views illustrating movement of the stent from the intermediate configuration to a deployed configuration using the medical device of FIG. 1;

DETAILED DESCRIPTION

Figures 1, 2:
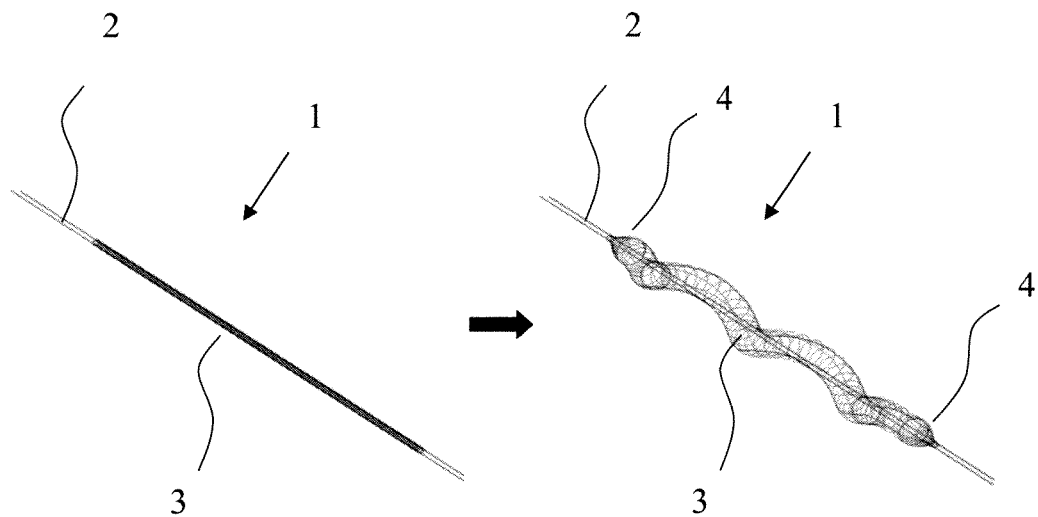
FIG. 1 is an isometric view of a medical device according to the invention in a collapsed configuration.
FIG. 2 is an isometric view of the medical device of FIG. 1 in an expanded configuration.
Figure 2A:
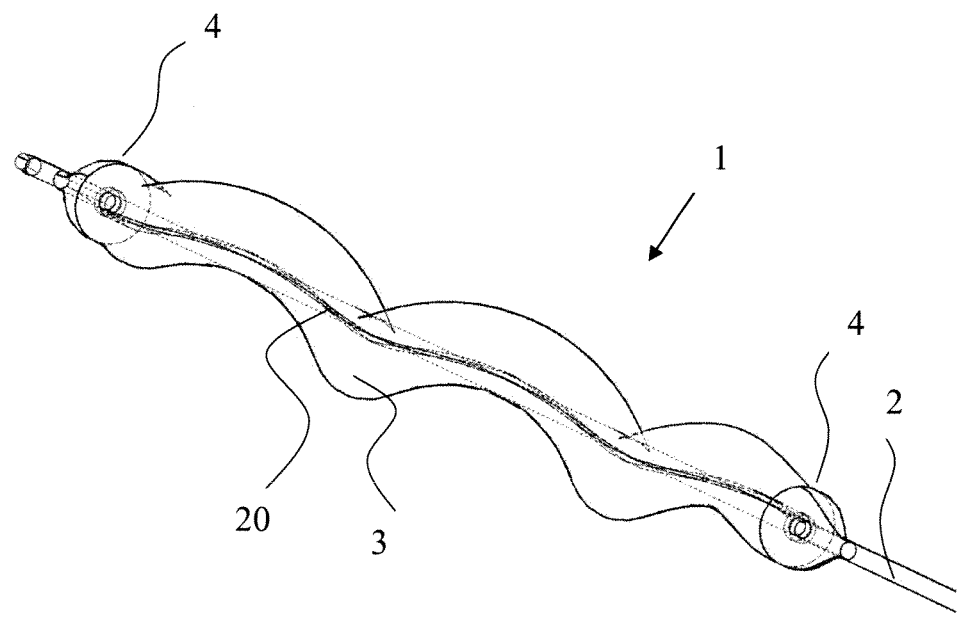
FIG. 2(a) is an isometric view of the medical device of FIG. 1 in the expanded configuration.

Referring to the drawings, and initially to FIGS. 1 to 2(a) thereof, there is illustrated a medical system according to the invention. In this case the medical system comprises a stent deployment system.

The stent deployment system comprises a stent deployment device 1, and a stent suitable for deployment in a blood vessel 5 to support at least part of the internal wall of the blood vessel 5.

The stent deployment device 1 comprises an elongate catheter shaft 2, and a single expandable element 3 for location in the blood vessel 5. The expandable element 3 is mounted on the catheter shaft 2.

In this case the expandable element 3 comprises an inflatable balloon. The inflatable balloon 3 is movable between a collapsed configuration (FIG. 1) and an expanded configuration (FIG. 2). In the collapsed configuration the longitudinal axis of the balloon 3 is straight, and the balloon 3 is cylindrically shaped. In the expanded configuration part of the longitudinal axis of the balloon 3 is curved in three-dimensional space, and part of the balloon 3 is helically shaped. The balloon has at each end an end part 4 in which the helical angle of the longitudinal axis of the end part increases in a direction away from the end of the balloon.

The balloon 3 is suitable for expanding the stent.

The stent may be a balloon expandable stent 6, as illustrated in FIGS. 3 to 10(e). Alternatively the stent may be a self-expanding stent 7, as illustrated in FIGS. 11 to 18.

Figure 10:
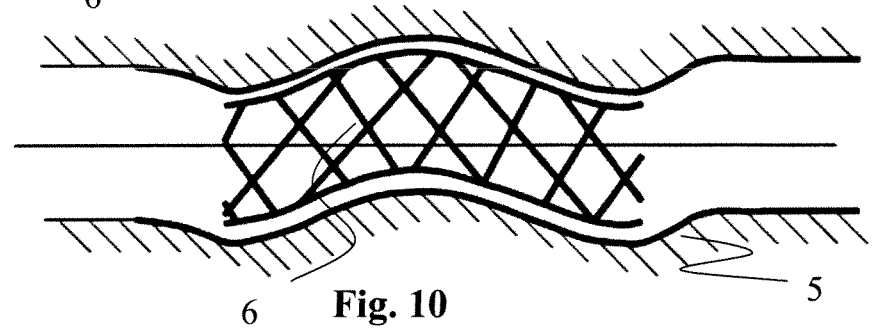

The stent 6, 7 may be movable from a collapsed delivery configuration (FIGS. 4 and 12) to a partially expanded intermediate configuration (FIGS. 6 and 14), and subsequently from the intermediate configuration to a fully expanded deployed configuration (FIGS. 10 and 18). In the delivery configuration the longitudinal axis of the stent 6, 7 is straight. In the deployed configuration the longitudinal axis of the stent 6, 7 is curved in three-dimensional space.

Figure 6:
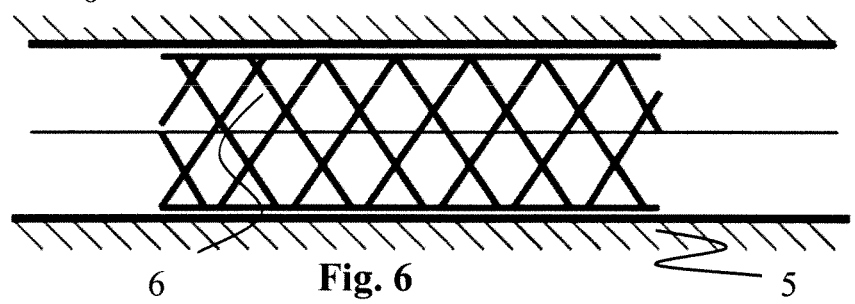

The longitudinal axis of the stent 6 may be straight in the intermediate configuration (FIG. 6). The balloon 3 is suitable for expanding the stent 6 having the straight longitudinal axis. In this case the balloon 3 expands the stent 6 to ensure that in the deployed configuration the longitudinal axis of the stent 6 is curved in three-dimensional space.

Figure 14:
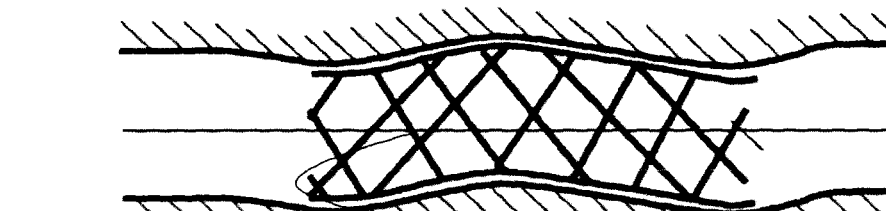

Alternatively the longitudinal axis of the stent 7 may be curved in three-dimensional space in the intermediate configuration (FIG. 14). The balloon 3 is suitable for expanding the stent 7 having the longitudinal axis which curves in three-dimensional space. In this case the balloon 3 expands the stent 7 to ensure that in the deployed configuration the stent 7 is bedded into the internal wall of the blood vessel 5 and the stent 7 has taken up the fully deployed three-dimensional curve. In addition the balloon 3 expands the stent 7 to ensure that the stent amplitude ratio is such that it is not possible for blood to flow through the blood vessel 5 or the stent 7 without undergoing swirling. The amplitude ratio is the ratio of the amplitude of the helical longitudinal axis of the stent to the internal diameter of the stent.

The balloon 3 is inflated to expand the stent 7 enhancing its helical structure, increasing the amplitude ratio, reducing the pitch, anchoring the stent 7 in place, and ensuring good wall apposition.

Figures 10A, 10B, 10C, 10D, 10E:
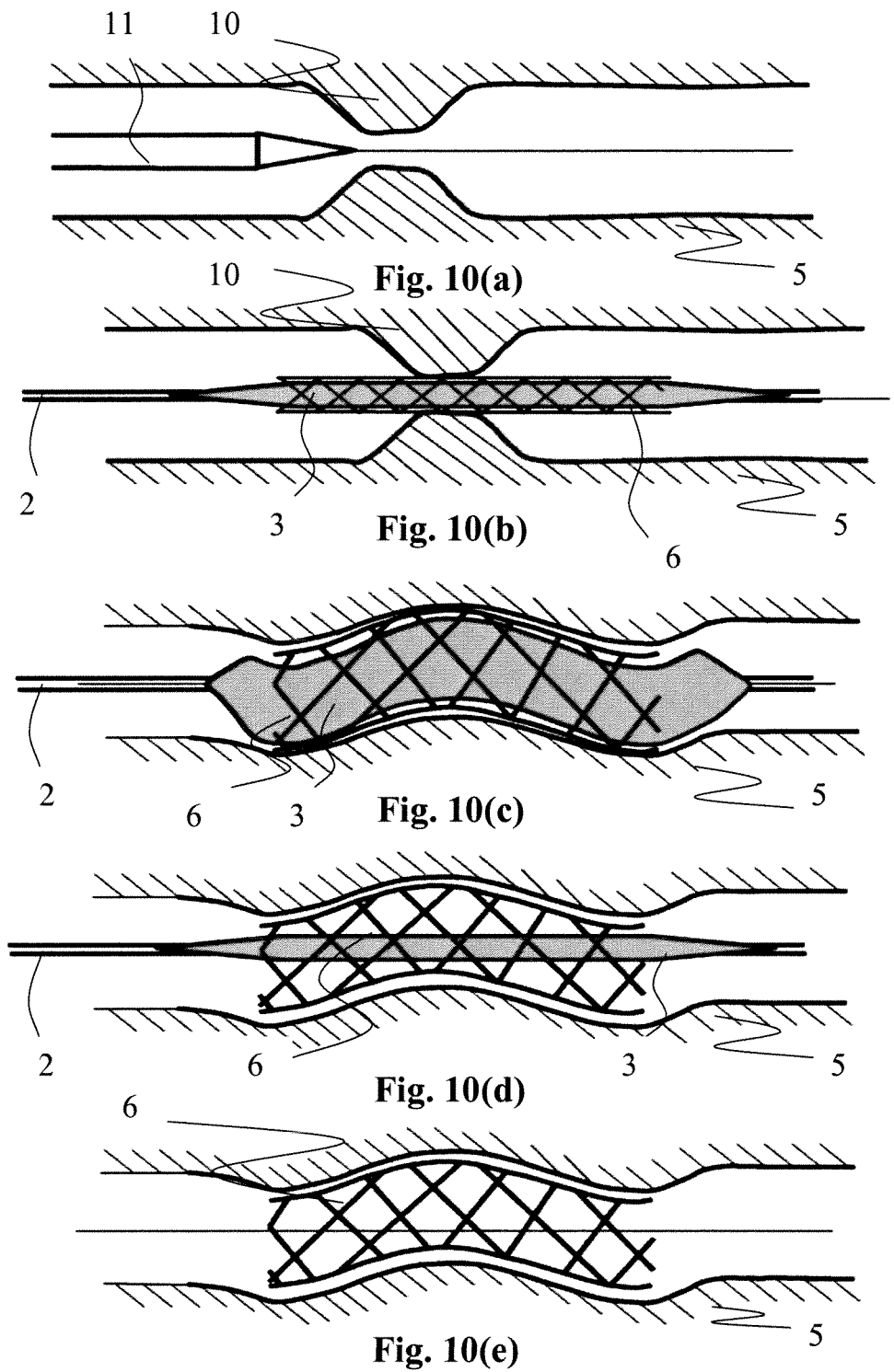
FIGS. 10(a) to 10(e) are cross-sectional side views illustrating movement of the stent of FIGS. 4 to 10 from the delivery configuration to the deployed configuration using the medical device of FIG. 1.

The stent 6 may be movable directly from the collapsed delivery configuration (FIG. 10(b)) to the fully expanded deployed configuration (FIG. 10(c)) without any intermediate configuration. In the delivery configuration the longitudinal axis of the stent 6 is straight. In the deployed configuration the longitudinal axis of the stent 6 is curved in three-dimensional space.

The balloon 3 is suitable for expanding the stent 6 having the straight longitudinal axis. In this case the balloon 3 expands the stent 6 to ensure that in the deployed configuration the longitudinal axis of the stent 6 is curved in three-dimensional space.

Figure 8:
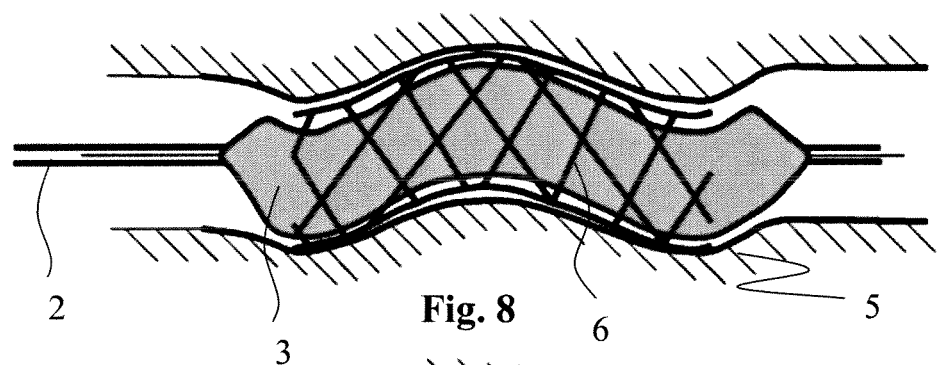

In each case the balloon 3 in the expanded configuration exerts force on the stent 6, 7. In the deployed configuration the stent 6, 7 in turn exerts force on the internal wall of the blood vessel 5 causing the longitudinal axis of the blood vessel 5 to curve in three-dimensional space (FIGS. 8 and 16).

As illustrated in FIG. 2(a), the stent deployment device 1 also comprises visualisation means to align the balloon 3 with the stent 6, 7. In this case the visualisation means comprises a marker 20 on the balloon 3. The marker 20 extends circumferentially and longitudinally along the balloon 3 in a helix or spiral. The marker 20 may be aligned with the helical shape of the stent 6, 7.

FIG. 2(a) illustrates the helical marker 20 on the helical balloon 3.

The stent deployment device 1 may be configured for rapid exchange delivery over a guidewire or over-the-wire delivery over a guidewire.

FIG. 1 illustrates the helical balloon 3 unexpanded on the catheter 2, and FIG. 2 illustrates the helical balloon 3 expanded on the catheter 2.

In use, the stent deployment device 1 may be used to deploy the balloon expandable stent 6 in the blood vessel 5 to support at least part of the internal wall of the blood vessel 5, as illustrated in FIGS. 3 to 10(e). Alternatively the stent deployment device 1 may be used to deploy the self-expanding stent 7 in the blood vessel 5 to support at least part of the internal wall of the blood vessel 5, as illustrated in FIGS. 11 to 18.

In one case the balloon expandable stent 6 is arranged in the delivery configuration mounted to a delivery catheter 8. In the delivery configuration the longitudinal axis of the stent 6 is straight. The delivery catheter 8 comprises an inflatable balloon 9.

Figure 4:
FIGS. 4 to 6 are cross-sectional side views illustrating movement of a stent from a delivery configuration to an intermediate configuration in the blood vessel of FIG. 3.
Figure 5:
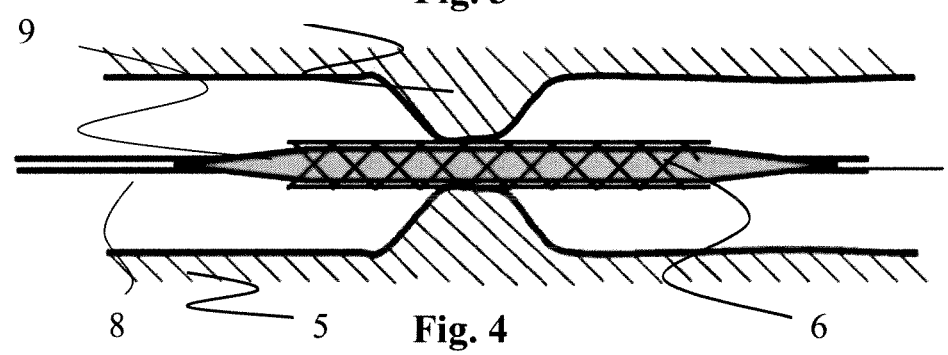

The balloon 9 is movable between a collapsed configuration (FIG. 4) and an expanded configuration (FIG. 5). In the collapsed configuration the longitudinal axis of the balloon 9 is straight, and the balloon 9 is cylindrically shaped. In the expanded configuration the longitudinal axis of the balloon 9 is straight, and the balloon 9 is cylindrically shaped.

The delivery catheter 8 and the stent 6 are inserted into the blood vessel 5 and advanced until the stent 6 is located at a desired treatment site 10 (FIG. 4). The balloon 9 is inflated to move the stent 6 from the delivery configuration to the intermediate configuration (FIG. 5). The longitudinal axis of the stent 6 is straight in the intermediate configuration. The balloon 9 is deflated and the delivery catheter 8 is withdrawn (FIG. 6).

Figure 7:
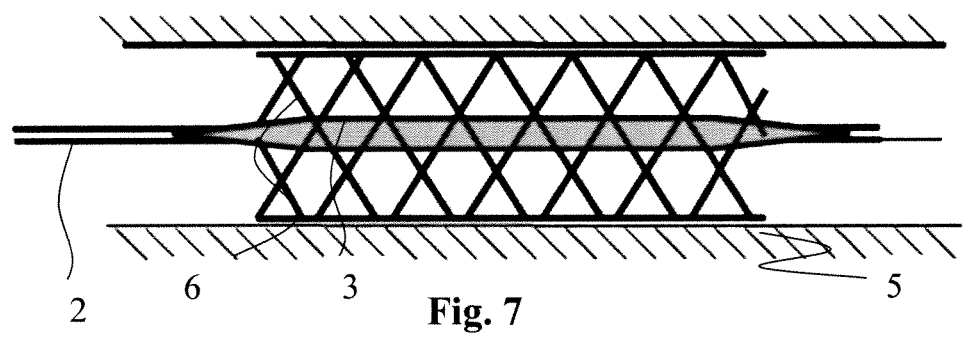
FIGS. 7 to 10 are cross-sectional side views illustrating movement of the stent from the intermediate configuration to a deployed configuration using the medical device of FIG. 1.

The stent deployment device 1 of the invention is then inserted into the blood vessel 5 and advanced until the balloon 3 is aligned with the stent 6 (FIG. 7). The balloon 3 is inflated to expand the stent 6 from the intermediate configuration to the deployed configuration. The balloon 3 in the expanded configuration exerts force on the stent 6 to move the stent 6 from the intermediate configuration to the deployed configuration (FIG. 8). In the deployed configuration the longitudinal axis of the stent 6 is curved in three-dimensional space. In the deployed configuration the stent 6 exerts force on the internal wall of the blood vessel 5 causing the longitudinal axis of the blood vessel 5 to curve in three-dimensional space.

The balloon 3 is deflated (FIG. 9), and the stent deployment device 1 is withdrawn from the blood vessel 5 (FIG. 10). The deployed stent 6 remains in the blood vessel 5.

Blood flowing through the three-dimensional curved blood vessel 5 undergoes a swirling action. The swirling flow of blood has been found to minimise thrombosis and platelet adhesion, and to minimise or prevent coverage of the stent 6 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

Figure 3:
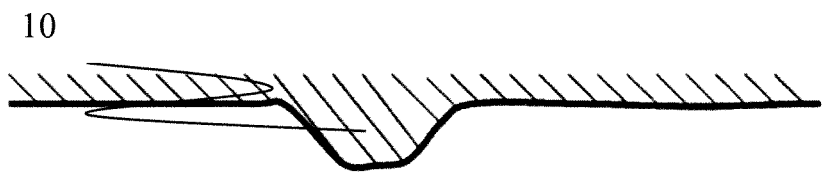
FIG. 3 is a cross-sectional side view of a blood vessel.
Figure 9:
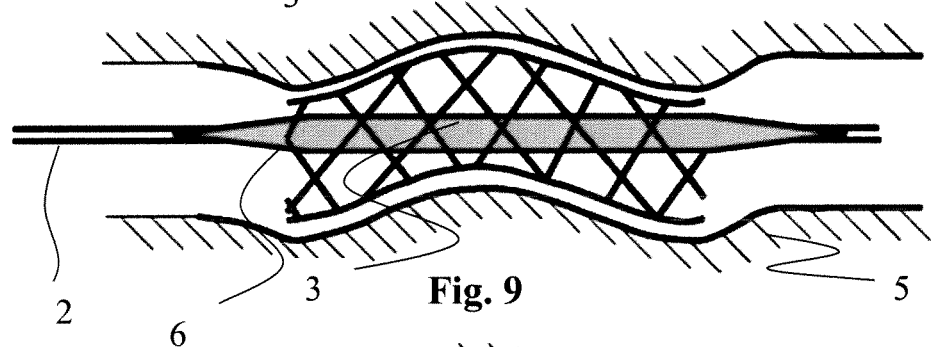

FIGS. 3 to 10 illustrate the balloon expandable straight stent 6 with the 3-D balloon 3. FIG. 3 illustrates the stenosed vessel 10. FIG. 4 illustrates the crimped stent 6 on the delivery system 8. FIG. 5 illustrates the balloon 9 inflated and the stent 6 deployed. FIG. 6 illustrates the vessel patency restored. FIG. 7 illustrates the 3-D balloon catheter 1. FIG. 8 illustrates the 3-D balloon 3 inflated. FIG. 9 illustrates the 3-D balloon 3 deflated for withdrawal. FIG. 10 illustrates the stent 6 and the blood vessel 5 deformed to assume the 3-D curvature.

In another case the balloon expandable stent 6 is arranged in the delivery configuration mounted to the stent deployment device 1 of the invention. In the delivery configuration the longitudinal axis of the stent 6 is straight.

The stent deployment device 1 and the stent 6 are inserted into the blood vessel 5 and advanced until the stent 6 is located at a desired treatment site 10 (FIG. 10(b)). The balloon 3 is inflated to expand the stent 6 from the delivery configuration to the deployed configuration (FIG. 10(c)). The balloon 3 in the expanded configuration exerts force on the stent 6 to move the stent 6 from the delivery configuration to the deployed configuration. In the deployed configuration the longitudinal axis of the stent 6 is curved in three-dimensional space. In the deployed configuration the stent 6 exerts force on the internal wall of the blood vessel 5 causing the longitudinal axis of the blood vessel 5 to curve in three-dimensional space.

The balloon 3 is deflated (FIG. 10(d)), and the stent deployment device 1 is withdrawn from the blood vessel 5 (FIG. 10(e)). The deployed stent 6 remains in the blood vessel 5.

Blood flowing through the three-dimensional curved blood vessel 5 undergoes a swirling action. The swirling flow of blood has been found to minimise thrombosis and platelet adhesion, and to minimise or prevent coverage of the stent 6 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

FIGS. 10(*a*) to 10(*e*) illustrate the straight stent 6 crimped onto the helical balloon 3.

In the case of the self-expanding stent 7, the stent 7 is arranged in the delivery configuration constrained within a delivery sheath 11. In the delivery configuration the longitudinal axis of the stent 7 is straight.

Figure 11:
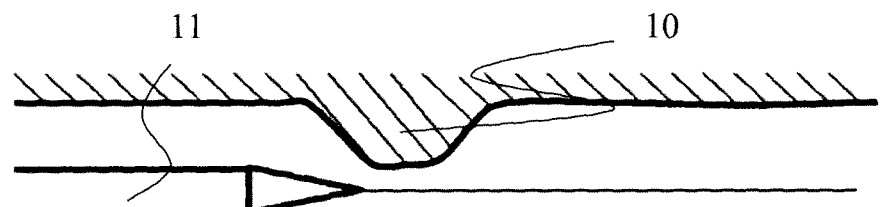
FIGS. 11 to 14 are cross-sectional side views illustrating movement of another stent from a delivery configuration to an intermediate configuration in the blood vessel of FIG. 3.
Figure 12:
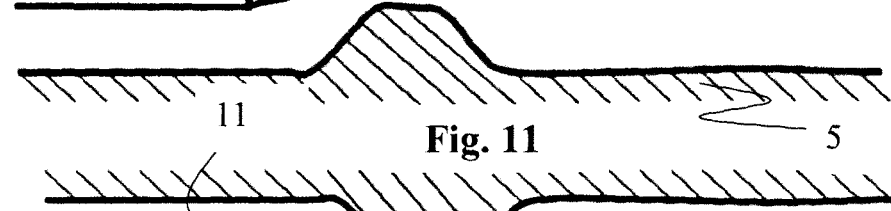
Figure 13:
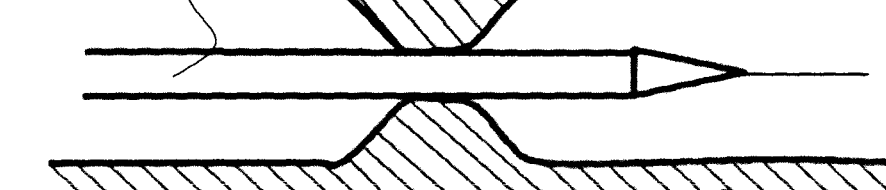

The delivery sheath 11 and the stent 7 are inserted into the blood vessel 5 and advanced until the stent 7 is located at the desired treatment site 10 (FIGS. 11 and 12). The sheath 11 is retracted to enable the stent 7 to move from the delivery configuration to the intermediate configuration (FIG. 13). The longitudinal axis of the stent 7 is curved in three-dimensional space in the intermediate configuration. In the intermediate configuration the stent 7 exerts force on the internal wall of the blood vessel 5 causing the longitudinal axis of the blood vessel 5 to curve in three-dimensional space. The delivery sheath 11 is withdrawn (FIG. 14).

The stent deployment device 1 of the invention is then inserted into the blood vessel 5 and advanced until the balloon 3 is aligned with the stent 7 (FIG. 15). The balloon 3 is inflated to expand the stent 7 from the intermediate configuration to the deployed configuration. The balloon 3 in the expanded configuration exerts force on the stent 7 to move the stent 7 from the intermediate configuration to the deployed configuration (FIG. 16). In the deployed configuration the longitudinal axis of the stent 7 is further curved in three-dimensional space. In the deployed configuration the stent 7 exerts further force on the internal wall of the blood vessel 5 causing the longitudinal axis of the blood vessel 5 to curve further in three-dimensional space.

The balloon 3 is deflated (FIG. 17), and the stent deployment device 1 is withdrawn from the blood vessel 5 (FIG. 18).

Blood flowing through the three-dimensional curved blood vessel 5 undergoes a swirling action. The swirling flow of blood has been found to minimise thrombosis and platelet adhesion, and to minimise or prevent coverage of the stent 7 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

FIGS. 11 to 18 illustrate the 3-D stent 7 with the 3-D balloon 3. FIG. 11 illustrates the stenosed vessel 10 and the stent delivery system 11. FIG. 13 illustrates the 3-D stent 7 deployed. FIG. 14 illustrates the blood vessel 5 remodelled to take the 3-D curvature. FIG. 15 illustrates the balloon catheter 1. FIG. 17 illustrates the 3-D balloon 3 deflated for withdrawal. FIG. 18 illustrates the balloon 3 withdrawn, and the stent 7 with maximised 3-D curvature in place.

Figure 19:
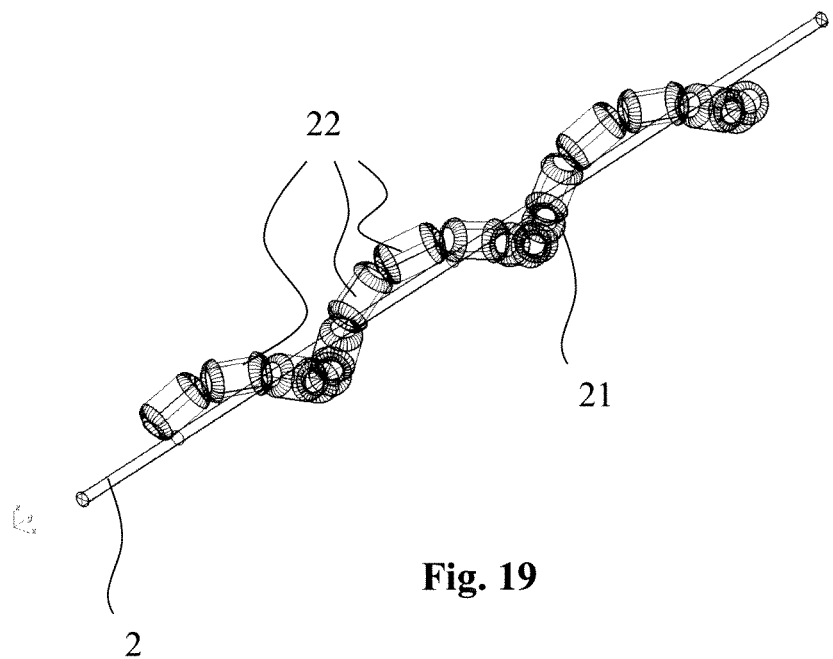
FIG. 19 is an isometric view of another medical device according to the invention in an expanded configuration.
Figure 20:
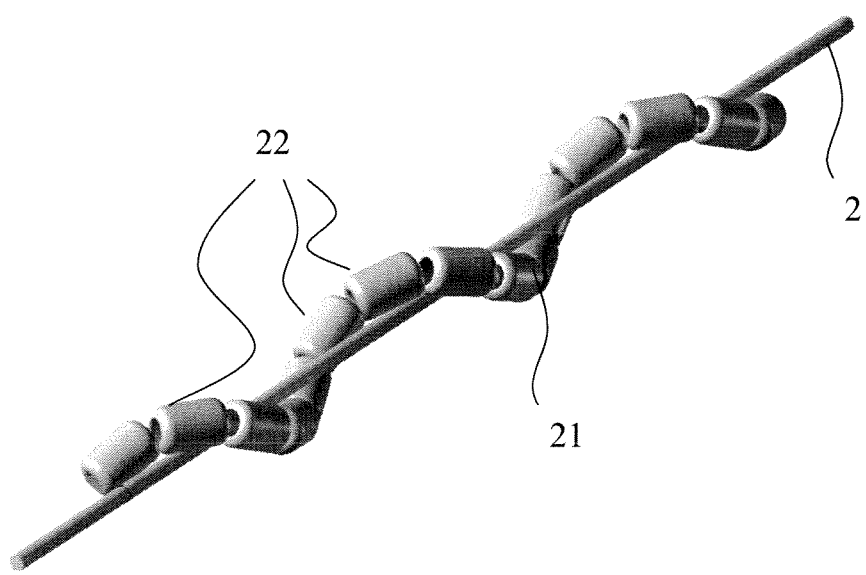
FIG. 20 is an isometric view of the medical device of FIG. 19 in the expanded configuration.

It will be appreciated that the expandable element 21 may comprise a plurality of separate expandable members 22, as illustrated in FIGS. 19 and 20. In the expanded configuration the overall longitudinal axis of the expandable element 21 is curved in three-dimensional space, and the expandable element 21 is helically shaped overall. In the expanded configuration the longitudinal axis of each expandable member 22 is straight, and each expandable member 22 is cylindrically shaped. The expandable element 21 has a piecewise three dimensional curved shape. FIGS. 19 and 20 illustrate the piecewise balloon 21 comprised of the plurality of straight balloons 22.

It will also be appreciated that the expandable element may have alternative shapes, for example in the expanded configuration part of the expandable element may be spiral shaped. The pitch of the spiral may be constant along the length of the expandable element, or may vary along the length of the expandable element.

It will further be appreciated that the stent deployment device may comprise a variety of possible visualisation means to align the expandable element with a stent.

Figure 21:
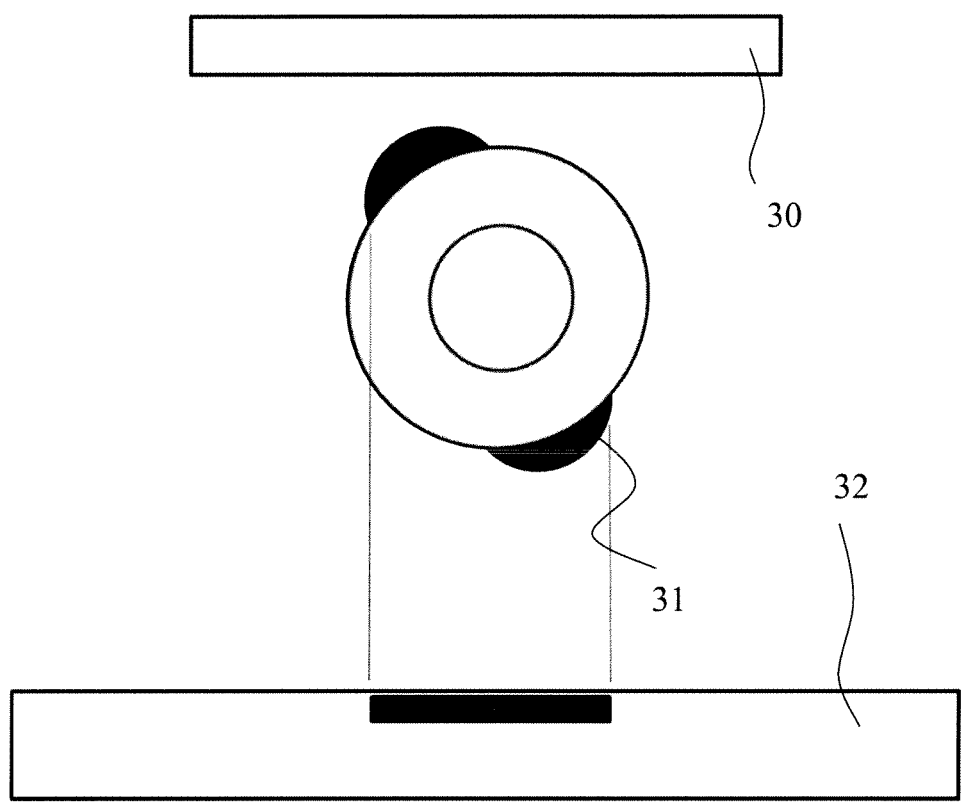
FIG. 21 is an end view of another medical device according to the invention in a non-aligned configuration.
Figure 22:
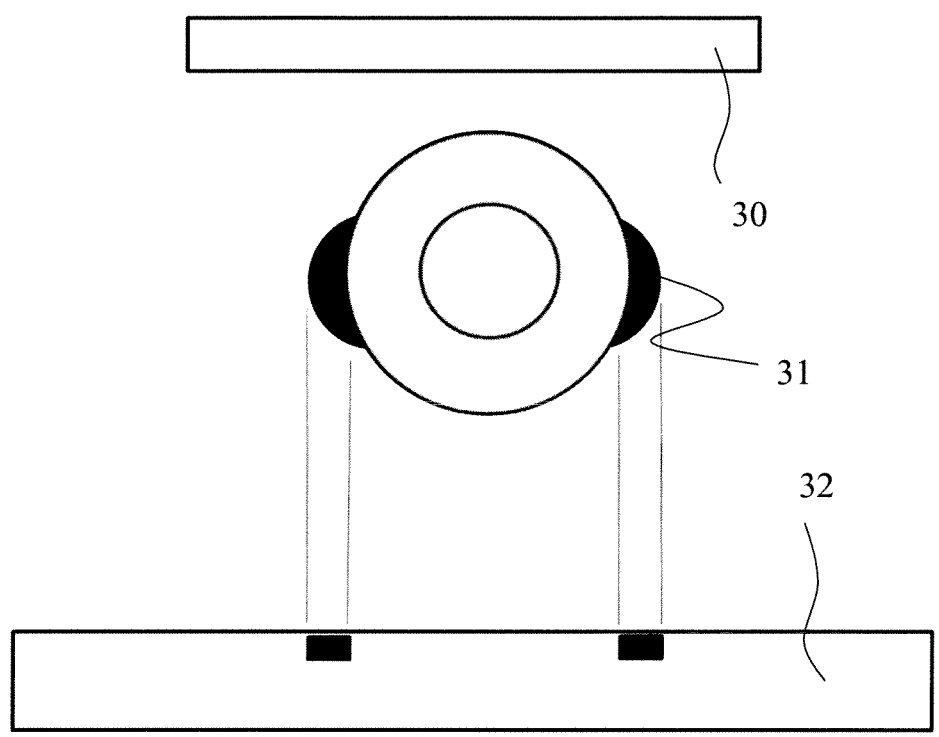
FIG. 22 is an end view of the medical device of FIG. 21 in an aligned configuration.
Figure 23:
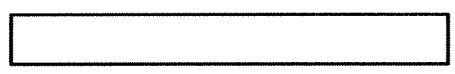
FIG. 23 is a side view of another medical device according to the invention in a non-aligned configuration.
Figure 26:
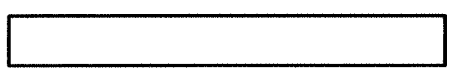
FIG. 26 is a side view of the medical device of FIG. 23 in an aligned configuration.
Figure 24:
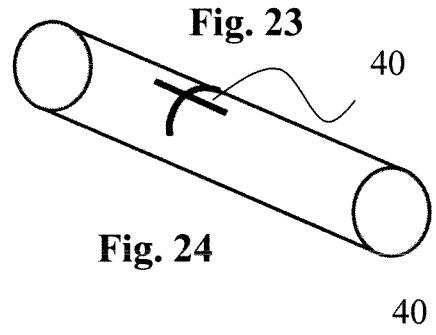
FIG. 24 is an isometric view of the medical device of FIG. 23 in the non-aligned configuration.
Figure 27:
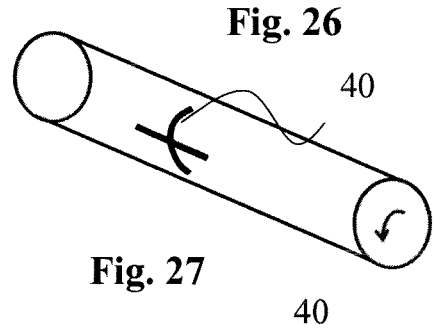
FIG. 27 is an isometric view of the medical device of FIG. 26 in the aligned configuration.
Figure 25:
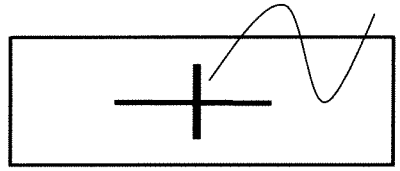
FIG. 25 is a plan view of the medical device of FIG. 23 in the non-aligned configuration.
Figure 28:
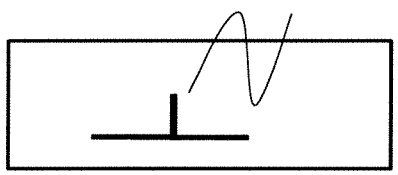
FIG. 28 is a plan view of the medical device of FIG. 26 in the aligned configuration.
Figure 29:
FIGS. 29 to 34 are views similar to FIGS. 23 to 28 of another medical device according to the invention.
Figure 32:
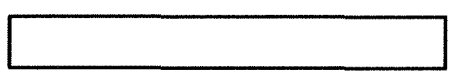
Figure 30:
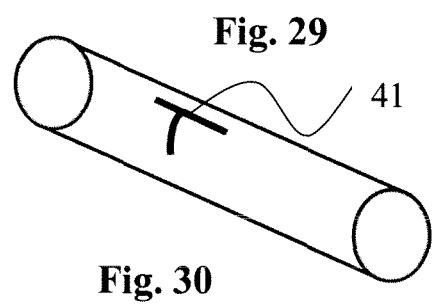
Figure 33:
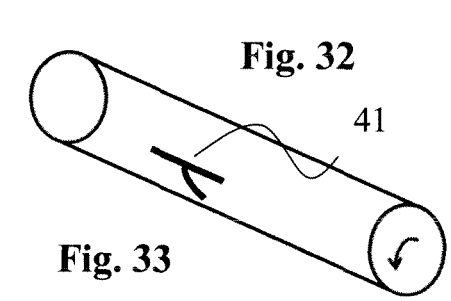
Figure 31:
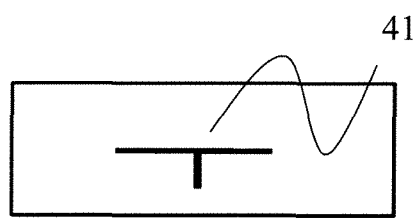
Figure 34:
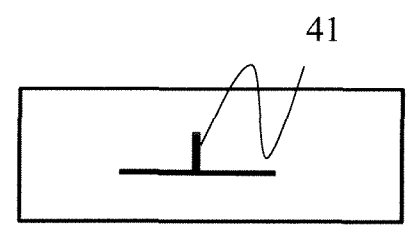

For example FIG. 21 illustrates a marker system before alignment. The system includes an x-ray source 30 and markers 31. FIG. 22 illustrates the constant mark on the imaging media 32 when the system has been aligned.

FIGS. 23 to 28 illustrate a cross shaped alignment marker 40 on a catheter. When viewed on the imaging media the marker 40 appears as a cross in the first orientation of the catheter. When the catheter is rotated into the correct alignment the marker 40 will appear as a T-shape. An x-ray source would be positioned at the top of the images.

FIGS. 29 to 34 illustrate a cross shaped alignment marker 41 on a catheter. When viewed on the imaging media the marker 41 appears as a 'T' in the first orientation of the catheter. After the catheter is rotated into the correct alignment the marker 41 will appear to have been rotated by 180 degrees. An x-ray source would be positioned at the top of the images.

It will also be appreciated that the medical system according to the invention may comprise a dilation system. The dilation system comprises a dilation device for dilating a blood vessel. The dilation device comprises the elongate catheter shaft, and the single expandable element for location in the blood vessel. In the expanded configuration the expandable element contacts the internal wall of the blood vessel directly.

The invention is not limited to the embodiments hereinbefore described, with reference to the accompanying drawings, which may be varied in construction and detail.

The invention claimed is:

1. A medical dilation device comprising:
   a balloon for location in a blood vessel,
   the balloon being inflatable between a collapsed configuration and an expanded configuration,
   in the expanded configuration at least part of the longitudinal axis of the balloon being curved in three-dimensional space, and
   wherein in the expanded configuration, the balloon is configured to directly contact the internal wall of the blood vessel wherein in the expanded configuration the balloon has a periphery which is configured to exert a force on the internal wall of the blood vessel over an entire circumference of the blood vessel causing the longitudinal axis of the blood vessel to curve in three-dimensional space.

2. A device as claimed in claim 1 wherein the device comprises a single balloon.

3. A device as claimed in claim 1 wherein in the collapsed configuration at least part of the longitudinal axis of the balloon is substantially straight.

4. A device as claimed in claim 1 wherein in the expanded configuration at least part of the balloon is substantially helically shaped.

5. A device as claimed in claim 1 wherein in the expanded configuration at least part of the balloon is substantially spiral shaped.

6. A device as claimed in claim 1 wherein the device comprises an elongate element upon which the balloon is mounted.

7. A medical system comprising:
   a medical device as claimed in claim 1, and
   a stent suitable for deployment in a blood vessel to support at least part of the internal wall of the blood vessel.

8. A system as claimed in claim 7 wherein the stent is movable between a delivery configuration and a deployed configuration.

9. A system as claimed in claim 8 wherein the stent is collapsed in the delivery configuration.

10. A system as claimed in claim 8 wherein in the delivery configuration at least part of the longitudinal axis of the stent is substantially straight.

11. A system as claimed in claim 8 wherein the stent is expanded in the deployed configuration.

12. A system as claimed in claim 8 wherein in the deployed configuration at least part of the longitudinal axis of the stent is curved in three-dimensional space.

13. A system as claimed in claim 8 wherein the stent is movable between the delivery configuration and an intermediate configuration, and between the intermediate configuration and the deployed configuration.

14. A method for treating a blood vessel, the method comprising the steps of:
   locating a balloon in the blood vessel,
   inflating the balloon from a collapsed configuration to an expanded configuration in which the balloon has a periphery and at least part of the longitudinal axis of the balloon is curved in three-dimensional space and in which the balloon periphery directly contacts an internal wall of the blood vessel around the entire circumference of the blood vessel, and
   the balloon exerts a force on the entire circumference of the internal wall of the blood vessel causing the longitudinal axis of the blood vessel to curve in three-dimensional space.

15. A medical device comprising:
   a balloon for location in a blood vessel;
   the balloon being inflatable between a collapsed configuration and an expanded configuration;
   in the expanded configuration at least part of a longitudinal axis of the balloon being curved in three-dimensional space;
   wherein the balloon has at each end a longitudinal end part; and
   wherein a longitudinal axis of each longitudinal end part has a helical angle that varies continuously along the length of the end part and which increases in a direction away from an end of the balloon.

16. A device as claimed in claim 15 wherein the balloon is configured to at least partially expand a stent.

17. A device as claimed in claim 15 wherein the device comprises one or more alignment elements to align the balloon with a stent.

18. A device as claimed in claim 15 wherein in the expanded configuration the balloon is configured to contact an internal wall of a blood vessel directly.

19. A method for treating a blood vessel, the method comprising the steps of:
   locating a balloon in the blood vessel; and
   inflating the balloon from a collapsed configuration to an expanded configuration in which at least part of the longitudinal axis of the balloon is curved in three-dimensional space;
   wherein the balloon has at each end a longitudinal end part; and
   wherein a longitudinal axis of each longitudinal end part has a helical angle that varies continuously along the length of the end part and which increases in a direction away from an end of the balloon.

20. A method as claimed in claim 19 wherein the step of inflating the balloon from the collapsed configuration to the expanded configuration at least partially expands a stent.

21. A method as claimed in claim 19 wherein the method comprises the step of aligning the balloon with a stent.

22. A method as claimed in claim 19 wherein the balloon contacts an internal wall of the blood vessel directly.

23. A medical dilation device comprising:
   a balloon for location in a blood vessel,
   the balloon being inflatable between a collapsed configuration and an expanded configuration,
   in the expanded configuration at least part of the longitudinal axis of the balloon being curved in three-dimensional space, and
   wherein in the expanded configuration, the balloon has a diameter which is identical to a diameter of an internal wall of the blood vessel so that the balloon is configured to directly contact the entire internal wall of the blood vessel,
   wherein in the expanded configuration the balloon is configured to exert a force on the entire internal wall of the blood vessel over an entire circumference of the blood vessel causing the longitudinal axis of the blood vessel to curve in three-dimensional space.

24. A method for treating a blood vessel, the method comprising the steps of:
   locating a balloon in the blood vessel,
   inflating the balloon from a collapsed configuration to an expanded configuration in which the balloon has a diameter and at least part of the longitudinal axis of the balloon is curved in three-dimensional space and in which the balloon diameter is identical to a diameter of an internal wall of the blood vessel so that the balloon directly contacts the entire internal wall of the blood vessel, and
   the balloon exerts a force on the entire internal wall of the blood vessel causing the longitudinal axis of the blood vessel to curve in three-dimensional space.

* * * * *

UNITED STATES PATENT AND TRADEMARK OFFICE
CERTIFICATE OF CORRECTION

PATENT NO. : 9,597,214 B2  
APPLICATION NO. : 12/249448  
DATED : March 21, 2017  
INVENTOR(S) : Kevin Heraty et al.

Page 1 of 1

It is certified that error appears in the above-identified patent and that said Letters Patent is hereby corrected as shown below:

On the Title Page

Insert --(73) Assignee: Veryan Medical Ltd., Horsham (GB)--

Signed and Sealed this  
Second Day of May, 2017

Michelle K. Lee  
*Director of the United States Patent and Trademark Office*